(12) United States Patent
Staeubli

(10) Patent No.: US 8,753,343 B2
(45) Date of Patent: Jun. 17, 2014

(54) BONE FIXING DEVICE

(76) Inventor: Hans Ulrich Staeubli, Muri (CH)

( * ) Notice: Subject to any disclaimer, the term of this patent is extended or adjusted under 35 U.S.C. 154(b) by 1017 days.

(21) Appl. No.: 11/722,404

(22) PCT Filed: Dec. 22, 2005

(86) PCT No.: PCT/CH2005/000768
§ 371 (c)(1),
(2), (4) Date: Jul. 5, 2007

(87) PCT Pub. No.: WO2006/066440
PCT Pub. Date: Jun. 29, 2006

(65) Prior Publication Data
US 2008/0154311 A1    Jun. 26, 2008

(30) Foreign Application Priority Data

Dec. 23, 2004    (CH) ........................................ 2143/04

(51) Int. Cl.
*A61B 17/72*    (2006.01)
(52) U.S. Cl.
USPC ............................................................. 606/62
(58) Field of Classification Search
USPC ........................................................ 606/62–68
See application file for complete search history.

(56) References Cited

U.S. PATENT DOCUMENTS

| | | | | |
|---|---|---|---|---|
| 3,709,218 A | * | 1/1973 | Halloran | 606/64 |
| 3,763,855 A | * | 10/1973 | McAtee | 606/64 |
| 3,842,825 A | * | 10/1974 | Wagner | 606/66 |
| 3,977,398 A | * | 8/1976 | Burstein | 606/62 |
| 4,091,806 A | * | 5/1978 | Aginsky | 606/63 |
| 4,101,985 A | * | 7/1978 | Baumann et al. | 623/22.46 |
| 4,467,793 A | * | 8/1984 | Ender | 606/62 |
| 4,473,069 A | * | 9/1984 | Kolmert | 606/64 |
| 4,506,662 A | | 3/1985 | Anapliotis | |
| 4,703,751 A | * | 11/1987 | Pohl | 606/62 |
| 4,733,654 A | * | 3/1988 | Marino | 606/64 |
| 4,794,918 A | * | 1/1989 | Wolter | 606/295 |
| 4,794,919 A | * | 1/1989 | Nilsson | 606/65 |
| 4,973,332 A | * | 11/1990 | Kummer | 606/65 |
| 5,122,141 A | * | 6/1992 | Simpson et al. | 606/62 |
| 5,356,410 A | * | 10/1994 | Pennig | 606/62 |
| 5,443,466 A | * | 8/1995 | Shah | 606/62 |
| 5,462,547 A | * | 10/1995 | Weigum | 606/65 |
| 5,562,557 A | * | 10/1996 | Ledvina et al. | 474/84 |

(Continued)

FOREIGN PATENT DOCUMENTS

DE    2459257    12/1975
DE    0689800    1/1996

(Continued)

*Primary Examiner* — Jerry Cumberledge
(74) *Attorney, Agent, or Firm* — Rankin, Hill & Clark LLP

(57) ABSTRACT

A bone fixing device includes an intramedullary nail (1) with a distal end part (2), a proximal end part (3), a center line (4), and a bore (5) that extends perpendicular to the center line (4) in the proximal end part (3) and is provided with a bore axis (6). The bone fixing device further includes a bone plate (10) with a top face (11), a bottom face (12) that is to be in contact with the bone, a continuous, central opening (13) which is located in the central portion of the bone plate (10) and connects the top face (11) to the bottom face (12), and several plate holes (14) that are also continuous and are disposed peripherally around the central opening (13).

40 Claims, 9 Drawing Sheets

(56) References Cited

U.S. PATENT DOCUMENTS

Figures 1C, 2A:
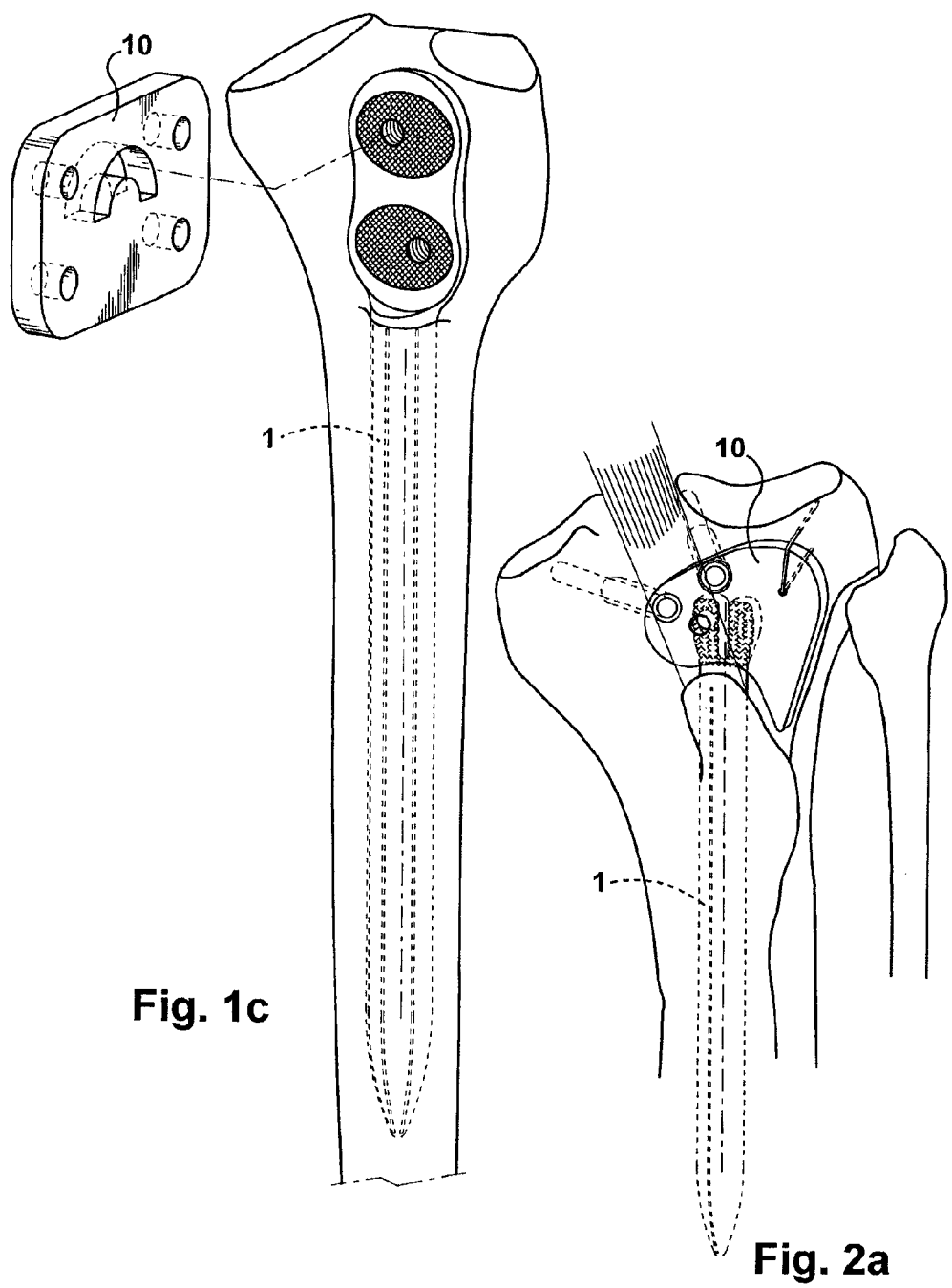

| | | | |
|---|---|---|---|
| 5,603,715 A * | 2/1997 | Kessler | 606/63 |
| 5,620,448 A | 4/1997 | Puddu | |
| 5,749,875 A | 5/1998 | Puddu | |
| 5,782,920 A * | 7/1998 | Colleran | 623/20.34 |
| 6,010,506 A * | 1/2000 | Gosney et al. | 606/62 |
| 6,019,761 A * | 2/2000 | Gustilo | 606/62 |
| 6,077,264 A * | 6/2000 | Chemello | 606/67 |
| 6,245,436 B1 * | 6/2001 | Boyle et al. | 428/472.2 |
| 6,270,499 B1 * | 8/2001 | Leu et al. | 606/64 |
| 6,338,734 B1 * | 1/2002 | Burke et al. | 606/281 |
| 6,527,775 B1 * | 3/2003 | Warburton | 606/62 |
| 6,767,351 B2 | 7/2004 | Orbay et al. | |
| 6,926,720 B2 * | 8/2005 | Castaneda | 606/98 |
| 2001/0012939 A1 * | 8/2001 | Wahl et al. | 606/67 |
| 2001/0021851 A1 * | 9/2001 | Eberlein et al. | 606/69 |
| 2002/0151898 A1 * | 10/2002 | Sohngen et al. | 606/62 |
| 2002/0193794 A1 * | 12/2002 | Taylor | 606/61 |
| 2003/0033019 A1 * | 2/2003 | Lob | 623/23.47 |
| 2003/0073999 A1 * | 4/2003 | Putnam | 606/62 |
| 2003/0083660 A1 | 5/2003 | Orbay | |
| 2003/0083661 A1 * | 5/2003 | Orbay et al. | 606/69 |
| 2003/0135212 A1 * | 7/2003 | Chow | 606/64 |
| 2003/0149486 A1 * | 8/2003 | Huebner | 623/19.11 |
| 2006/0100623 A1 * | 5/2006 | Pennig | 606/64 |
| 2010/0063504 A1 * | 3/2010 | Munro et al. | 606/64 |

FOREIGN PATENT DOCUMENTS

| | | | | |
|---|---|---|---|---|
| DE | 7519604 | | 6/2007 | |
| EP | 689800 | * | 1/1996 | |
| FR | 2614524 | * | 11/1988 | |
| FR | 2785518 | | 5/2000 | |
| GB | 2299941 | * | 10/1996 | |
| JP | 11047170 A | * | 2/1999 | A61F 2/28 |
| RU | 2206290 | * | 6/2003 | |
| WO | WO 9109571 A1 | * | 7/1991 | A61B 17/58 |
| WO | 99/20195 | | 4/1999 | |
| WO | 02/080790 | | 10/2002 | |

* cited by examiner

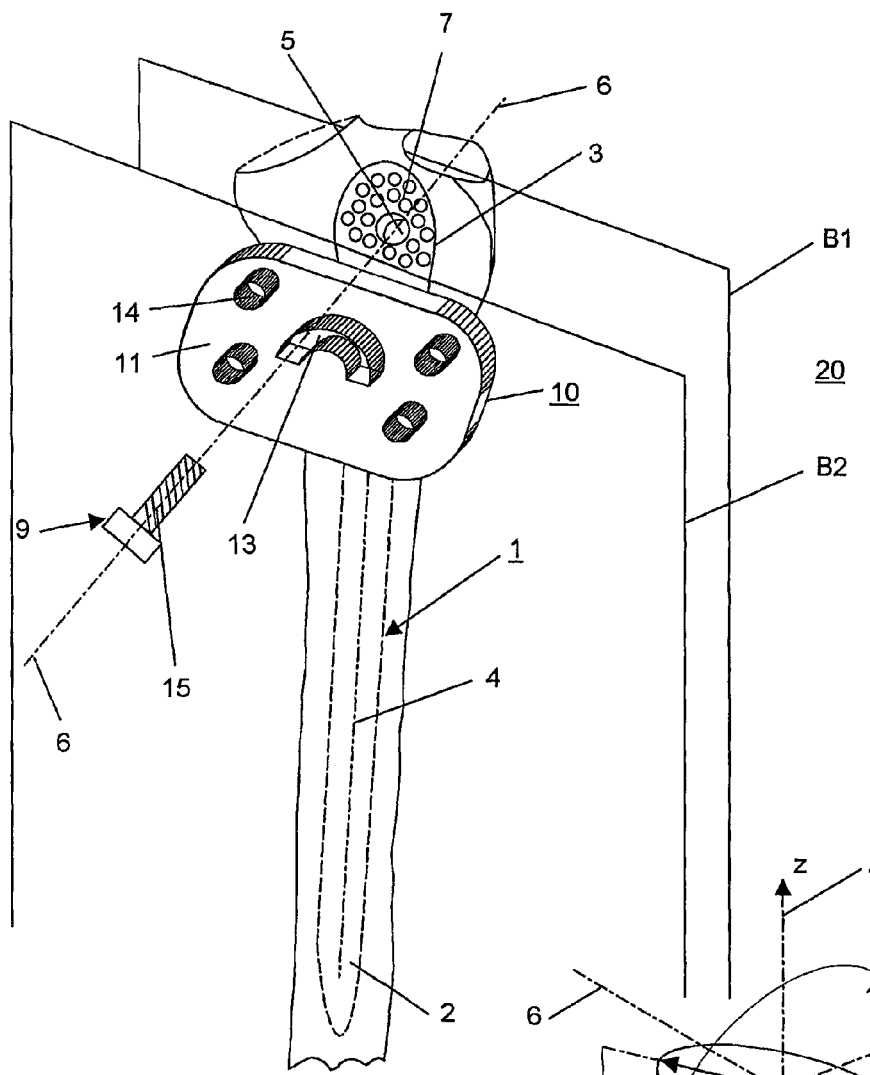
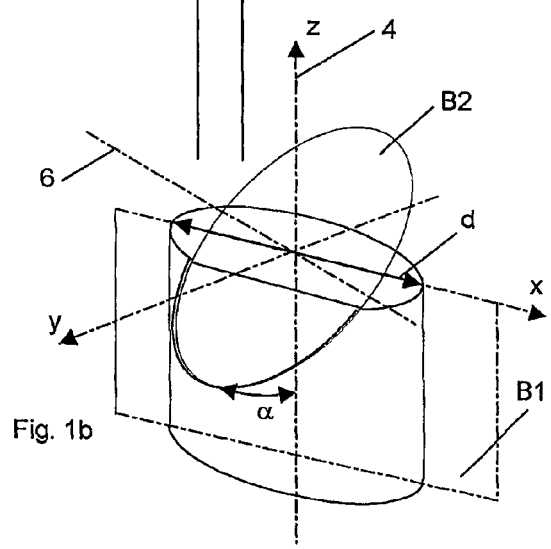
Fig. 1a
Fig. 1b

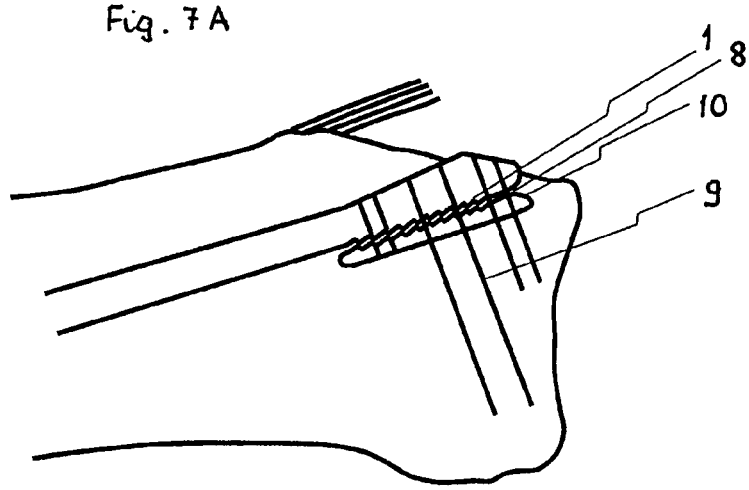
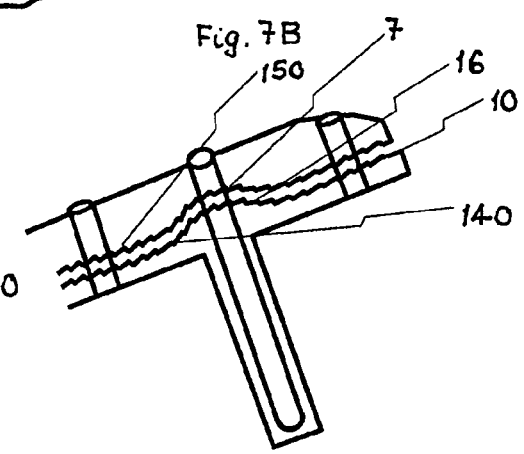
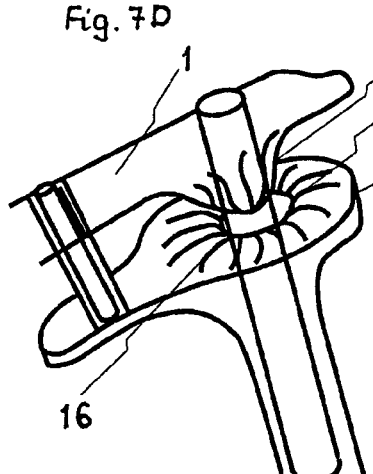
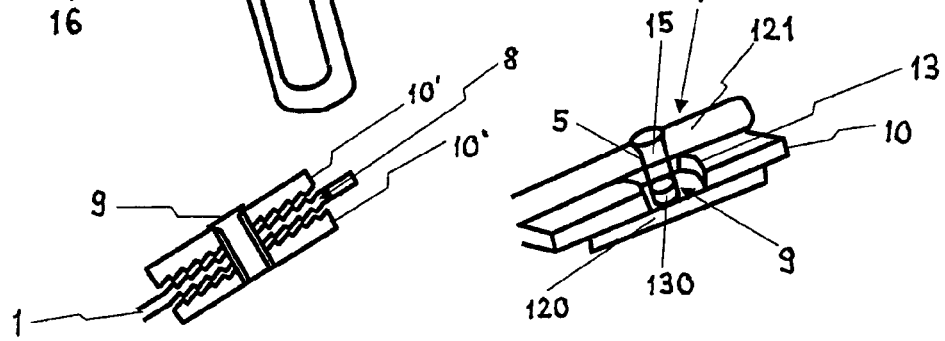

BONE FIXING DEVICE

The invention refers to a bone fixing device according to the main concept of the patent claim 1.

The bone fixing device according to the invention is in the following especially described for an application on the tibia.

Various techniques are known for performing a high tibial osteotomy. The distinction is in principle between so-called high tibial osteotomies of a laterally falling shut and medially falling open type. The English locution speaks of a "high tibial osteotomy lateral closing wedge" and "medial opening wedge" The French locution speaks of an "ostéotomie du tibia d'ouverture interne" or "d'addition interne". Apart from these classic forms of osteotomy, half-shaft osteotomies with reciprocal splinter inlays, spline-type osteotomies and various forms of tuberosita osteotomies are also performed.

In order to fix the high tibial osteotomy lateral closing wedge, according to the state of the art T- or L-shaped plates, so-called reconstruction plates, gable plates, cover plates, adjusted half-tube plates, TomoFix plates as well as fixateurs externes are used in different variants. Aron Hofmann from Salt Lake City, Utah described an oblique cutting template and an L-shaped plate to fix the high tibial osteotomy laterally closing wedge under the designation "Natural-Knee-Family High Tibial Osteotomy System".

For the fixing of high tibial osteotomy medial opening wedges various systems are used: the "Bone Plate System for Opening Wedge Proximal Tibial Osteotomy" according to U.S. Pat. No. 5,620,448, and the "Bone Plate System for Proximal Tibial Osteotomy" according to U.S. Pat. No. 5,749,875.

The publication "Open Wedge High Tibial Osteotomy With Rigid Plate Fixation" by Loberhoffer et de Simoni et Alex Staubli, Techniques in Knee Surgery 1(2):93-105, 2002 described a bone plate applied in order to stabilize the high tibial medial opening wedge to the antero-medial tibial face of the proximal tibia.

In 1988 Rab published the obliquely rising tibial osteotomy in children affected by Blount's disease, see "Oblique Tibial Osteotomy for Blount's Disease", J. Pediatr. Orthop. 8:715-720, 1988.

Sanoullier Jean Louis and Rosa Thierry in France published a lengthened, proximally t-shaped osteotomy plate with interchangeable wedges for the internal supporting of the high tibial osteotomy medial opening wedge according to FR 2,785,518.

Leone James et al. published a U.S. Pat. No. 6,767,351 on a T-shaped plate system with multi-directional fixing rods.

In order to fix the corrective osteotomy medial opening wedge, external fixators are also used.

Ito et al. Published in 2001 an improved locking nail for the intramedullary fixation of an osteoporotic bone, ref. J. Orthop Trauma 2001; 15; 192-196.

For the endomedullary fixation of tibial shaft and proximal tibial fractures in adults, an article "Bündel-Nagelungen" (Bundled Nails) was published in a nomograph in 1961 by K. H. Hackenthal, Berlin, Göttingen. Additional intramedullary nail techniques are: the classic tibia-nailing in the technique according to Küntscher, the conventionally bored tibia nailing, the different variants of the static and dynamic locking nailings according to Grosse/Kempf as well according to the recommendations of Zimmer GmbH (Ltd) (formerly Sulzer Medica, Centerpulse), and the elastic nailing using Prevost-, Metsiau or Nancy nails in children. The characteristic of these intramedullary nailing techniques is in general a transligamentary access through a longitudinal splitting of the ligamentum patellae by stripping off Hoffa's fatty tissue body with residual disorders in the connecting area of the stretching apparatus on the tuberositas tibiae, heterotopic ossifications and shrinkings of the patellar ligament with a consequent painful patella infera or patella baja (depression of the patella) and bending as well as stretching failure of the knee joint. In rare cases, a Sudeck dystrophy of the patella or of the trochlea femoris with a shrinking of Hoffa's fatty tissue body or of the ligamentum patellae occurs as a complication.

In typical fashion, the endomedullary power transmitters, which have a dorsally convex curvature in the proximal part of the tibial intramedullary nail, are introduced into the tibia above the tuberositas tibiae using a transligamentary access. For its locking various proximal, medial and distal locking fixation devices are known.

The German interpretation patent DE 2.459.257 described a distal disc-like flattened nail, characterized in that a number of nail ends are superimposed on each other.

The German Patent DE 7.519.604 described an intramedullary nail whose end deviates from the usual round shape, in order to introduce forces and rotating moments.

The EP 00669048 disclosed an elastic femoral intramedullary nail designed in a concave manner, so as to receive a convex fixation device designed in a T-shape and fitted with round reception openings.

The EP-8 1 024 782 LEU et al describes an endomedullary nail with a plate-like attachment, that rotates a rotation axis extending approximately perpendicularly to the nail axis in any position with respect to a bottom plate resting on the bone, and can be fixed by using fixing elements. The attachment set up coaxially with the intramedullary nail is therefore likewise disposed in an intramedullary manner, and can therefore be rotated around the common axis only coaxially to the intramedullary nail. Moreover, in this LEU et al. device, a bone plate resting on the bone is missing.

The U.S. Pat. No. 5,603,715 by KESSLER describes a device with a hollow intramedullary nail, which carries at it proximal end a ring gear set up orthogonally to the nail axis. The device also comprises a bone plate with a bushing set up perpendicularly to the plate, whose free end carries a ring gear corresponding to the intramedullary nail. By using a connecting screw passed through the bushing in the hollow intramedullary nail, the bone plate can be fixed to the intramedullary nail in any desired position. The disadvantage of this device is that its ability to rotate coaxially to the longitudinal axis of the nail is limited, such that the bone plate enters the area of the joint and hinders its function. A further disadvantage is the fact that this already known plate is shown as being emplaced on the humerus in a position proximal to the soft tissues, meaning on the rotating collar, with the risk of a limited motion of the shoulder joint thus equipped, and of a consequent rigidity of the shoulder. A device fitted with a hollow intramedullary nail, designed in its central section to be a straight line and rigid construction, is practically incapable of being inserted, from a distal point, into the narrow intramedullary hollow of a bone provided with a narrow intramedullary hollow like that of the humerus bone shown here. For this reason, humerus shaft fractures are fitted with elastic, small diameter intramedullary nails made of a flexible titanium alloy (Prevost or Nancy nails).

The invention intends to provide a remedy in these cases. The object of the invention is to create a bone fixing device capable of affecting both the bone as well as the soft tissue structures to a lesser degree.

The invention solves the assigned task through a bone fixing device offering the characteristics of claim 1, as well an implant offering the characteristics of claim 41.

The advantages secured by the invention are essentially to be seen in the fact that thanks to the bone fixing device according to the invention:

a) An extra-articular and extra-ligamentary emplacement (meaning outside and in a sub-ligamentary position under the ligamentum patellae, but not through the knee-cap ligament) of the implant is possible, which leads to a careful treatment of the stretching mechanism and in particular of the ligamentum patellae as well as of the tuberositas tibiae, b) The knee joint and in particular the tibia can be operated in a slightly bent position, which considerably simplifies the repositioning of the fragments and the implantation of the fixing device, while carefully treating the soft tissues.

c) No important translating forces and rotational moments are exerted on the upper, median and lower endomedullary boundaries of the elements of the intramedullary bone channel;

d) The soft tissue mantle normally covering the bone, and in particular the stretching mechanism including the ligamentum patellae and Hoffa's fatty tissue body during the implantation/explantation operation and the fixation are essentially treated carefully;

e) A flexing of the knee up to 110° as well as a splitting of the ligamentum patellae can be prevented.

f) Possible corrections of the relative positions of the bone fragment positions, as defined by the endomedullary and extramedullary fixing devices of the main bone fragments capable of being shifted with respect to each other, are made possible between each other to a defined extent;

g) The bone fragment corrections achieved between each other in the corrected position up to the end of the healing process of the bone and up to the reconstituted transversal bone structure can be held in a fixable condition;

h) Later after-corrections, if needed, can be achieved by simple manipulations;

i) Neuro-vascular complications can be avoided;

j) The periosteal bone fracture healing in a meta-diaphyseal shaft area of the bone is treated carefully;

k) A broad bone supporting action in an out-of center position with respect to the central intramedullary space, capable of treating the soft tissues carefully, can be attained;

l) A plurality of bone fixing means of the bone fixing device guarantees a versatile fixability in an epi-meta-diaphyseal bone area;

m) Contrary to the EP-B1 024 762 LEU et al, no interference between a nail head section set up in a central axial position and in the soft tissues arises; and n) No damage of the stretching mechanism occurs, thus preventing the feared patellar depression.

In contrast with the conventional high tibial osteotomy medial opening wedges, a medial soft tissue access at a high tibial level is unnecessary. The pes anserinus tendons, the lateral medial ligament and the rear oblique ligament are treated carefully, and a nerve damaging action of the ramus infrapatellaris of the nervus saphenus is prevented. The typical increase of the dorsal slope of the high tibia in the sagittal plane ("increased posterior slope") as well as the possible patellar depression such as observed in the intraligamentary osteotomy of the medially falling open type is eliminated. A medial soft tissue access can be avoided.

In contrast to the high tibial osteotomies laterally falling shut, the detaching of the antero-lateral muscular system from the anterolateral tibial crest is unnecessary. The calf bone need not be osteotomized. The possibility of damaging the nervus peroneus extending under the calf bone head is eliminated; a compartment syndrome of the anterolateral muscle lodge is highly unlikely. The typical slope of the so-called joint line of the knee joint in the frontal plane, such as observed after a lateral closing wedge osteotomy, as well as the insufficiency of the capsular ligament (arcuatum complex) are eliminated.

This allows a corresponding correction of the axes, the lateral displacement and the length of the tibia, and stabilizes the fracture and osteotomy fragments of the tibia in line with the axis, as well as in a torsion- and bend-proof manner, after a completed correction of the same, securely until the time of a full healing of the bone. The premise for this result is a properly prepared, biomechanically load resistant and fixed-angle attachable, material-controlled, endosteal basic implant, consisting of suitable upper, middle and lower sections as well as of an instrument and a positioning set befitting the same.

The endosteal fixing elements of the upper sections, the intermediate connecting element, the distal, endomedullary fixing element as well as the tibia-transfixing fixation elements are designed to an anatomically correct scale, vary in accordance with the outer and inner affected high tibial, and follow the external geometry and internal architecture of the tibia and the configuration of its corresponding, internal medullary hollows.

The intermediate go-between element is in turn designed with a torsion-resistant mechanism as well as with a suitable fine-toothing system, preferably equivalent to a rotating pin or rotating plate, and connected to the lower endomedullary fixing device (endomedullary power transmitter EMKT) in such a manner that an axial correction, a lateral displacement in a typical range from 0 mm up to half width as well as a correction in length of 0-3 cm is possible. The distal endomedullary fixing element adapted to the inner shape of the medullary channel can be connected, after the end of the correction, with the proximal fixing elements in the capsular membrane in an unbending, torsion- and bend-proof manner. The implantable structure bridging the fracture- and osteotomy area, consisting of proximal medullary membrane fixing elements, intermediate connecting systems and distal, endomedullary fixed fixing elements, forms a functionally stable unit up to the moment that the healing of the tibial bone fracture/tibial bone osteotomy is formally completed.

The proximal fixing elements are essentially fixed in the internal architecture of the proximal, central and lateral high tibial on the capsular membrane side. The intermediate fixing element adapted to the same is detached from the underlying periosteum by small irregularities and projections, and follows in its adapted shape the external geometry of the high tibial, while respecting the attachment geometry to be left intact and the substance of the attachment of the stretching mechanism (ligamentum patellae) on the tuberositas tibiae, as well as the attachment geometry of the tractus iliotibialis on the Gerdy tuberculum. The intermediate fixing element can also be partially or wholly sunk into the high tibial from the ventral side. The intermediate connecting element is in turn connected to the distal, endomedullary power transmitter, and preferably designed as a torsion-proof mechanism, typically with a tri-dimensional, finely toothed rotating pin/rotating plate construction capable of guaranteeing a stable anchoring of the fixing elements. Another connecting variant is designed as a hinge.

The distal anchoring is done by using special transossal connecting and/or locking fixing devices, to be eventually completed by elastic fixing nails inserted and integrated in the basic implant. The orthopedic/traumatologic, endosteal, endomedullary basic implant allows, in connection with appropriately adapted instruments and a positioning system befitting the same, a biomedically adequate fixing of the fracture- and osteotomy fragments through a minimally invasive, the soft tissues carefully treating access. For an additionally careful treatment of the soft tissues, an especially adapted, endomedullary bone separating system is available, which avoids damaging the capsular membrane by using vibrating saw blades conventionally applied from the outside, and is therefore conducive to a endosteal bone healing process. The assembly and disassembly of the endosteal, endomedullary basic implant is based on a simple design. The arising bone defects are, after the orthopedic/traumatologic basic implant is provided with been removed in a manner carefully treating the soft tissue, left open or filled without interstices with suitable bone replacing materials.

The bone fixing system appropriately comprises a compression device capable of pressing the clamping faces on the nail side and on the plate-side against each other.

The compression device typically includes an internal thread in the bore of the intramedullary nail and a setscrew that can be passed through the central opening of the bone plate and screwed into the inner thread of the bore.

In a special form of embodiment, the intramedullary nail is fitted with two clamping faces on the nail-side. This execution allows a proximal section of the intramedullary nail to be optionally fixed below or above the bone plate. In specific cases, the two nail-side clamping faces can be set up in an essentially asymmetric, out-of-center position with respect to the center line.

In yet another form of embodiment, the nail-side clamping face is shaped in a planar form and defines a plane B2, which forms an angle alpha in the range from 0° to 30°, preferably from 10° to 20°, with the plane B1 defined by the center line and the diameter d of the intramedullary nail running parallel to the plane B2.

Alternatively, a plane B2 set up orthogonally to the bore axis can form an angle in the range of 0° to 30°, preferably of 10° to 20°, with a plane B1 defined by the center line and the diameter d of the intramedullary nail (1) running parallel to the plane B2.

In a further alternative a plane B2 set orthogonally to the bore axis can extend parallel to a plane B1 defined by a diameter d extending through the center line and parallel to the plane B2.

In a special form of embodiment the nail-side clamping face is set in the area of the intramedullary nail's bore.

The plate-side clamping face can be conformed either only on the lower side or only on the upper side of the bone plate, or both on the lower side as well as on the upper side. In a further variant, the plate-side clamping face can be conformed inside the bone plate and run essentially parallel to its upper and lower side. In this embodiment the nail-side clamping face is inserted into the U-shaped bone plate and at that point, after the clamping has been completed, surrounded by the bone plate in a sandwich manner. The U-shaped bone plate can in this case be fitted inside the U with one or even two clamping faces, and the same also applies to the intramedullary nail, which can also have one or two clamping faces, such that in this embodiment two pairs of clamping faces can be opposing each other, a situation that improves the clamping face and therefore the clamping action.

In a special form of embodiment the plate-side clamping face can be formed in the area of the bone plate opening. The center line can cross the nail-side clamping face under an average angle of 1°-20°, preferably of 2°-10°.

In an additional form of embodiment the proximal end part of the intramedullary nail can be conformed as a separate, modular construction element.

In another form of embodiment an intermediate element made of a plastically deformable material can be set up between the clamping faces corresponding to each other. This allows preventing the so-called "fretting corrosion".

In a special form of embodiment the intramedullary nail can be curved in an asymmetrical, multiplanar manner. Thanks to its multiplanar, asymmetrical curvature, the intramedullary nail can in this embodiment be inserted into the intramedullary hollow and in the intramedullary space without difficulty.

The clamping faces of the intramedullary nail and of the bone plate corresponding to each other can each be conformed spherically or cylindrically. The fixing faces matching in their form allow in this case a mutual correction in the direction of the six degrees of freedom (6DOF), meaning around the three rotational axes: flexion/extension, abduction/adduction, internal rotation/external rotation, and along the three translating planes: anterior translation/posterior translation, medial translation/lateral translation and compressing plane/distracting plane; this occurs to the desired degree but at the same time with a certain boundary.

The clamping faces are advantageously provided with a tri-dimensional structure, preferably in the form of toothed systems. This allows relative angular displacements and relative translations between the intramedullary nail and bone plate, and after performing the angular displacements and translations to a desired position, for instance through a setscrew, a fixing to each other in a geometrical or power form. The toothed systems can for instance take the form of rounded threads, pyramidal tips or multi-layered polygons. The toothed faces can also be hardened, coated and/or anodically spark-anodized (in specific cases, by using anodic spark anodization II). The toothed faces can also be designed in a concave or convex manner, and/or conformed to corresponding multiplanar faces or congruent arcs.

The distal intramedullar nail terminal can advantageously by rounded in a parabolically symmetrical manner. The intramedullary nail can also have nine longitudinal grooves arranged in a parallel planar manner, in order to achieve rotational stability.

The distal end of the intramedullary nail can also be split in a longitudinal direction. This conformation serves to prevent a concentration of stresses at the nail end, depending on the transligamentary access and on the subsequent fatty tissue cicatrization.

The bone plate can have a concavely curved lower side. This achieves an optimum adaptation to the bone face.

The bone plate can also have a convexly curved upper side. This allows a simple production of the curved plate from a planar plate.

In another form of embodiment the lower side and/or the upper side may be curved in a spherical manner, which also results in a simplified production.

In a particular form of embodiment, the lower side of the bone plate has a groove with a groove bottom forming the plate-side clamping face, a first and a second lateral wall. The groove is provided with a minimum width b between the first and the second lateral wall, which allows the proximal end part of the intramedullary nail to be at least partially received in the area of the nail-side clamping face, such that the nail-side clamping face can come to rest against the plate-side clamping face. The groove allows a lateral boundary of the motion of the intramedullary nail relative to the bone plate during the implantation, which means an auxiliary position for the operator in assembling the implant. The proximal nail terminal of the intramedullary nail in the area of the nail-side clamping face advantageously has a width of B>b. The advantage of this embodiment lies in the fact that the lateral displaceability can be selected by choosing the construction elements.

In a further form of embodiment the bone fixing device comprises at least one bone fixing element having a longitudinal axis (25). The at least one bone fixing element can advantageously be arranged such that the projections of its longitudinal axis in the X,Z plane, the X,Y plane and the Y,Z plane of a tri-dimensional coordinate system enclose an angle with the axes x, y, z relative to the x-axis (in the X, Y plane), to the z-axis (in the X, Z plane) and to the z-axis (in the Y, Z plane) of between 0° and 60°, where the z-axis runs coaxially to the center line (4) of the intramedullary nail (1) in the area of the nail-side clamping face (7), and the x-axis runs orthogonally to the z-axis and coaxially to the diameter d of the intramedullary nail (1) running parallel to the plane (2).

In an intramedullary nail with a curved center line, the z-axis can be formed by the tangent to the center line (4) in the point of intersection of the center line (4) with the bore axis (6) forming the axis of rotation.

The face of the construction elements of the bone fixing device, in particular of the intramedullary nail, of the bone plate and of eventual bone fixing elements can be spark-anodized (preferably by anodic spark-anodization II). This achieves an increased mechanical strength and a microbiocidal effect. The face of the construction elements can also be provided with a microbiocidal coating—preferably containing silver ions.

As already mentioned, the intramedullary nail can be conformed in an asymmetrical manner. In this case, the intramedullary nail can have a first curvature in a first (frontal or latero-medial) plane, and a second curvature in a second (sagittal or antero-posterior) plane set up perpendicularly to the first plane.

In addition, the bone fixing device can comprise one or more of the following construction elements as bone fixing elements: a pushing screw, a pulling screw, a compressing screw, and a set screw.

The intramedullar nail can also have a continuous channel.

In another form of embodiment the bone fixing elements are conformed as intramedullary space-crossing wires.

The bone fixing elements can also comprise bushings which are pressed into receptacles in the bone plates, and whose central bores allow bone screws to pass through.

In a further form of embodiment, the bone fixing device is conformed as an implant for the fixing of bones in an endosteal and endomedullary space, especially of tibial fractures, tibial osteotomies, high tibial fractures or high tibial osteotomies, and in this case comprises:

A) at least an upper section (23) that can be anchored in the epiphyseal, metaphyseal and/or diaphyseal area of a bone;

B) at least a lower section (21) that can be anchored in the epiphyseal, metaphyseal and/or diaphyseal area of a bone; and C) at least a middle section (22) which is suitable for connecting the at least one upper section (23) with the at least one lower section (21) and can be anchored in the epiphyseal, metaphyseal and/or diaphyseal area of a bone.

The upper section can comprise one, preferably several bone fixing elements. The upper section can also comprise at least one lateral bone fixing element (L), at least one central bone fixing element (Z) and at least one median bone fixing element (M). The at least one bone fixing element can comprise a bushing (26) with a central bore, and a bone screw capable of being passed through the central bore.

The at least one bone fixing element can comprise a bone screw.

The upper endosteal lateral fixing element (L) in the lateral high tibial can follow the individual tibia configuration in respect to the orthogonal alignment in the sagittal and coronary plane, and suitably enclose, from the ventral inlet region of the endosteal lateral fixing device (L), in an axial deviation in the axial plane in such a manner of a suitable positioning sector, an angle alpha in respect to the antero-posterior zero alignment, of 0 to 25 degrees toward the center and of 0 to 25 degrees to the side, and preferably an angle alpha of from 0 to 5 degrees set up toward the center and the side.

The upper, endosteal lateral fixing device (L) can be aligned, in reference to the sagittal slope of the tibial plateau and in reference to the antero-posterior alignment axis, in the sagittal plane in a suitable positioning sector at an angle aeta of 0 to 25 degrees in a cranial direction as well as at an angle aeta of 0 to 45 degrees in a caudal direction, and in reference to the sagittal ligament axis of the endomedullary power transmitter, at a sagittal angle aeta of 0 to 110 degrees, preferably of 0 to 25 degrees, at a sufficient distance of at least 1-3 mm to the immediately subchondral, tibia-side areas of the medial and lateral femoro-tibial joint compartment as well as to the joint area of the proximal tibio-fibular joint and to the areas intercondilaris anterior and intercondilaris posterior of the high tibial epiphysis.

The upper, lateral endosteal fixing device (L) with at least one upper epi-, meta-, and diaphyseal lateral (L), central (Z), medial (M) fixing device of the upper section, the upper section with at least one middle epi-, meta-, and diaphyseal middle section, and the middle section with at least one lower diaphyseal, endosteal, exomedullary membrane, endomedullary fixing element of the lower section can be designed as being connected in a suitable manner.

The upper, endosteal, lateral fixing device (L) with at least one endosteal, lateral (L), central (Z), medial, (M) endosteal, exosteal and endomedullary fixing device can be stably connected in a suitable manner, independently of the fact on whether axial, longitudinal or angular corrections have been performed.

The upper endosteal lateral (L), central (Z), medial (M) epi-, metaphyseal endosteal fixing devices can be connected with at least one distal, endomedullary, exomedullary, endosteal, exosteal applied fixing device (lower section of the orthopedic, traumatological basic implant) can be connected in a axially, longitudinally and angularly stable way in a suitable manner.

The upper, at least one endosteal lateral epi-metaphyseal fixing device (L) can be suitably connected with a typically similarly conformed central (Z) and medial (M) epi-, meta-, and diaphyseal endosteal fixing device, the endomedullary central fixing device can be designed, in reference to an antero-posterior orientation- or zero axis in the axial plane, as forming an angle beta of 0 to 25 degrees in a central direction as well as an angle beta of 0 to 45 degrees in a lateral direction, and in the sagittal plane, in reference to the antero-posterior zero-axis, as forming an angle deviation aeta of 0 to 25 degrees in a cranial direction and an angle deviation aeta of 0 to 25 degrees in a caudal direction.

The endosteal, lateral fixing device (L) and the endosteal central fixing device (Z) designed for the lateral (L) or for the central fixing device (Z) can be connected with at least one endosteal medial (M) fixing device, the endosteal, medial fixing device (M) can be designed, in reference to a zero-axis generally oriented at an angle of 45 degrees to the antero-posterior axis of the tibia, as forming an angle gamma of 0 to 45 degrees in a ventral direction up to an angle gamma of 0 to 45 degrees in a dorsal direction, and in a sagittal plane, in reference to an antero-posterior zero-axis, as forming an angle deviation aeta of 0 to 25 degrees in a cranial direction and an angle deviation aeta of 0 to 25 degrees in a caudal direction.

The endosteal lateral (L) and the endosteal central (Z) fixing element can be designed for the lateral (L) or for the central (Z) endosteal fixing element; the endosteal medial fixing device (M) can be designed, in reference to a ventro-dorsally oriented zero-axis, as forming an angle delta of 0 to 20 degrees toward the central sector boundary and an angle delta of 0 to 75 degrees up to the ventral sector boundary.

The endosteal fixing elements can be designed from at least two central and at least two medial, or from at least two lateral and at least two medial fixing devices, each of which is introduced from a ventral, paraligamentary endosteal direction more or less oriented in an antero-posterior direction, whose zero-axes form in a medial direction an angle epsilon, and in a lateral direction an angle zeta.

The central (Z) and medial (M) endosteal, epi-, meta-, and diaphyseal fixing devices can be designed as being connected through a suitable device with at least one middle, intermediate (I) and with at least one lower diaphyseal, endosteal and endomedullary fixing device.

The intermediate fixing devices can, if designed as midsections, be designed between the single endosteal lateral (L), endosteal central (Z) and endosteal medial (M) fixing elements of the upper section and the endomedullary fixing elements of the lower section (of the distal, endomedullary power transmitter), as being typically bendable against each other at an angle of 0 to 30 degrees, displaceable toward any side by 0 to one half of a tibial width, displaceable in length by 0 to 3 cm and, after a successfully performed correction, again as being stably connectible with each other in an ideal position.

The endosteal epi-, meta- and diaphyseal fixing devices can consist of tubes, elements of tubes, cylinders, elements of cylinders, bushings, elements of bushings, rods, elements of rods, plates, elements of plates, flaps, elements of flaps, nails, bolts, screws, laminas, elastic nails, T and U-shaped profiles, multiple edge elements and locking bolts, locking nails, fixed screws, bendable screws, bolts or other fixing devices. In a preferred embodiment, guide bushings and rod-like elements fixed inside the same can in the upper area of the tibia be designed with an intermediate fixing device (I), preferably a base plate, and fastened in the upper middle and distal area of the tibia with endomedullary (D) fixing elements preferably designed in a bent form.

The intermediate fixing devices (I) that connect the endosteal, epi-metaphyseal fixing devices with the meta-, dia- and epiphyseal endomedullary fixing devices can consist of elements adapted from the outer and inner architecture of the high tibial and its face as well as from the adjacent soft tissues, which are preferably designed as supporting plates with a mutually engaging toothed construction, as hinged devices, as rotating plate or rotating pin elements, and as ball- and rod type elements.

The intermediate fixing device or the mid-section designed as a bone plate or base plate (BP), which is oriented toward the front face of the high tibial and typically fitted with rises and projections turned toward the bone, can be supported at a distance from 0.1 to 4 mm, suitably cover and embrace the frontal tibia boundary up to maximally the lateral (outer) rim of the high tibial, laterally and above the tuberositas tibiae, behind and next to the ligamentum patellae and its attachment area in the central area of the high tibial (apophysis) all the way up to the medial, rounded high tibial face, and be designed as a base fixing plate for the suitable endosteal, endomedullary fixing devices.

The base plate can be sunken up to a third (generally from 1 to 33%), up to two thirds (generally from 34 to 66%) or up to over two thirds (generally from 67 to 100%) into the ventral area of the high tibial, and be designed, in reference to the center of the tuberositas tibiae, in a radius of 5 to 50 mm, with a distance of at least 0.1 mm to the attachment of the ligamentum patellae.

The base plate can cover the para-ligamentary lateral and medial faces of the tibia and the frontal high tibial face lying centrally under the ligamentum patellae, and technically enable the insertion of at least one fixing element introduced in a para-ligamentary manner from the ventral side.

The base plate can also have a fixing element that is directly integrated in the base plate and fixed in an endosteal manner in the upper lateral (L), central (Z) or median area of the high tibial.

In a further form of embodiment, the endomedullary fixing element can be fixed in a torsion-proof manner around a central fixing mechanism, where the fixing elements of the base plate are designed as slot-like receiving openings for the upper and lower fixing of the endomedullary power transmitter in the base plate.

The base plate and the endomedullary fixing element can be designed as finely toothed rotating pins or rotating plate mechanisms that guarantee the stable fixation of the endomedullary power transmitter with the base plate, independently of an eventually needed correction of the position of the fragments (refer to the FIGS. 6A, 6B, 6C, 6D, 6E).

The upper lateral (L), central (Z) and medial (M) epi-meta diaphyseal fixing devices can, after the necessary displacement between each other, be suitably designed to be capable of being connected to each other at fixed angles and in a non-displaceable manner.

The lower endomedullary fixing device can be suitably firmly connected with the intermediate fixing device of the base plate and preferably be designed as a sector of a sphere fitted with a second congruent spherical sector element such that angular corrections are possible and held in a fixed position in a suitable fixing manner.

The endomedullary fixing device and the endomedullary power transmitter (EMKT) designed for the stabilization of tibial fractures and tibial osteotomies can proximally provide at least one supporting plate, which is integrated in the EMKT and designed for a paraligamentary and retroligamentary endosteal fixation.

The endomedullary lower fixing device can, in its extension toward the distal main fragment, be designed with suitable fixing devices for an endomedullary, endosteal, exosteal and transossary fixation. The endomedullary power transmitter (EMKF) can be suitably connected with the distal and proximal tibial main fragment though suitable fixing devices, and after completing the relative positioning change of the tibial main fragments against each other, again be designed to be suitably resistant against angular changes, torsions and partial loadings.

The bone fixing device according to the invention is particularly suitable for performing a process for an endosteal and endomedullary fixation of bones, in particular of tibial fractures, tibial osteotomies, high tibial fractures and high tibial osteotomies, where appropriate bone weakenings for a plastic formability of the bone are produced in at least three different planes of the bone to be treated. The weakening of the bone can be produced by drilling or sawing. At the same time of weakening of the bone, autologous, structured bone material can be recovered.

Figure 2B:
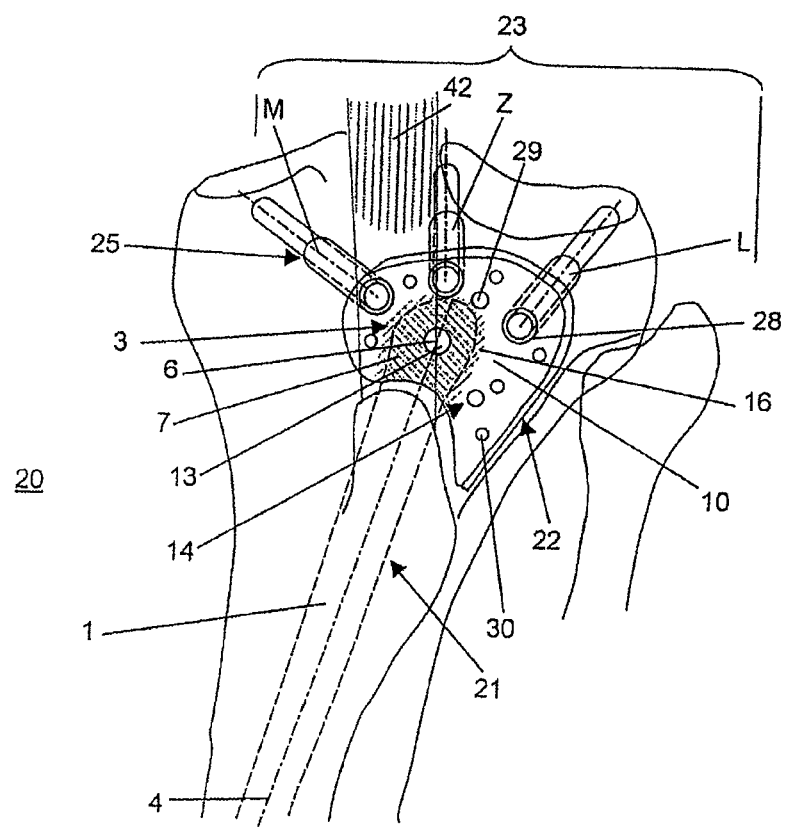
Figure 3:
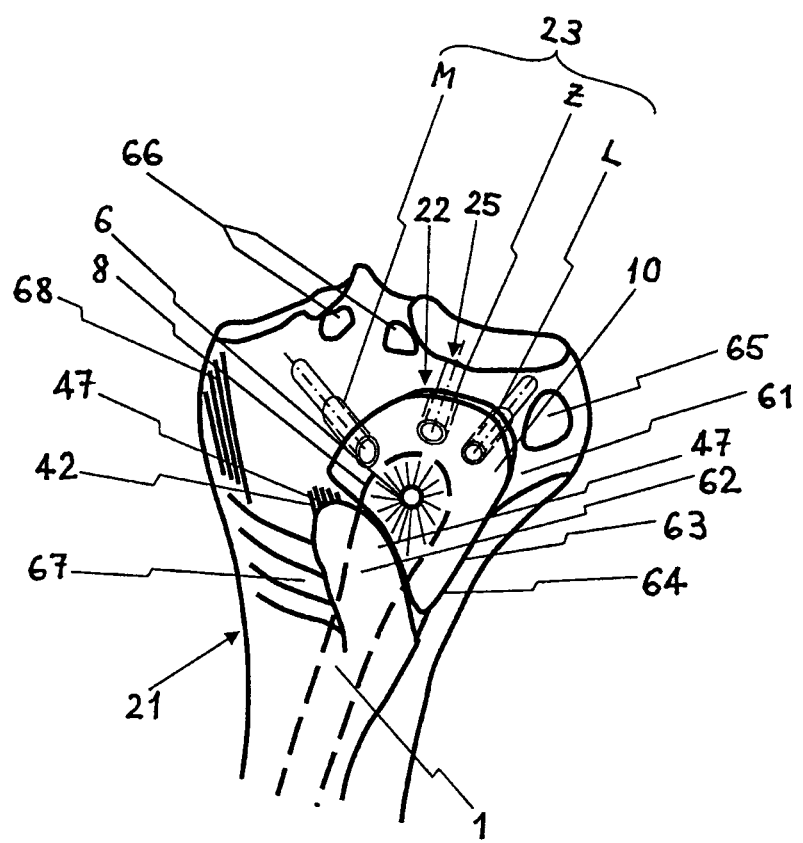
Figures 4A, 4B, 4C:
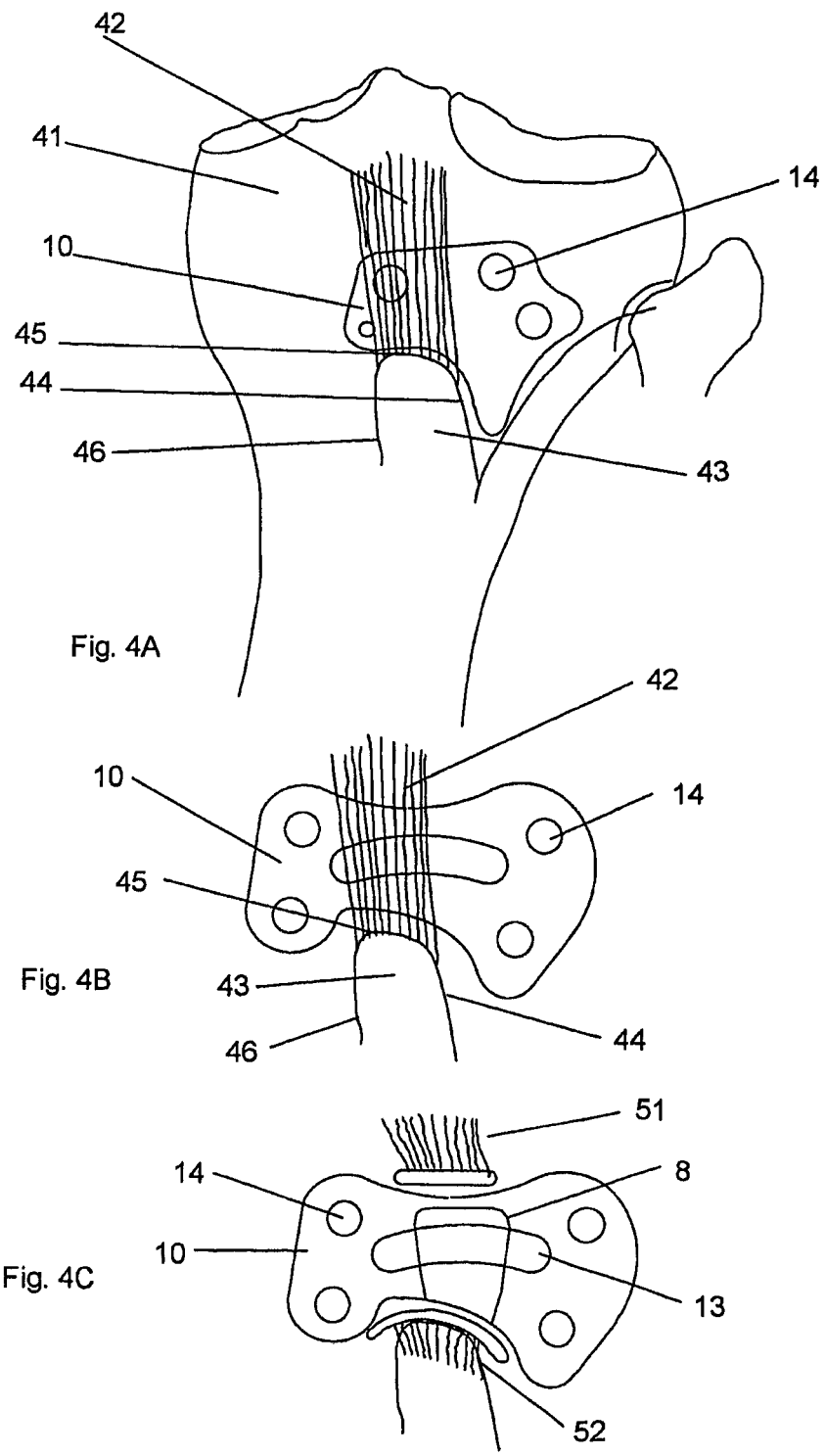
Figure 6:
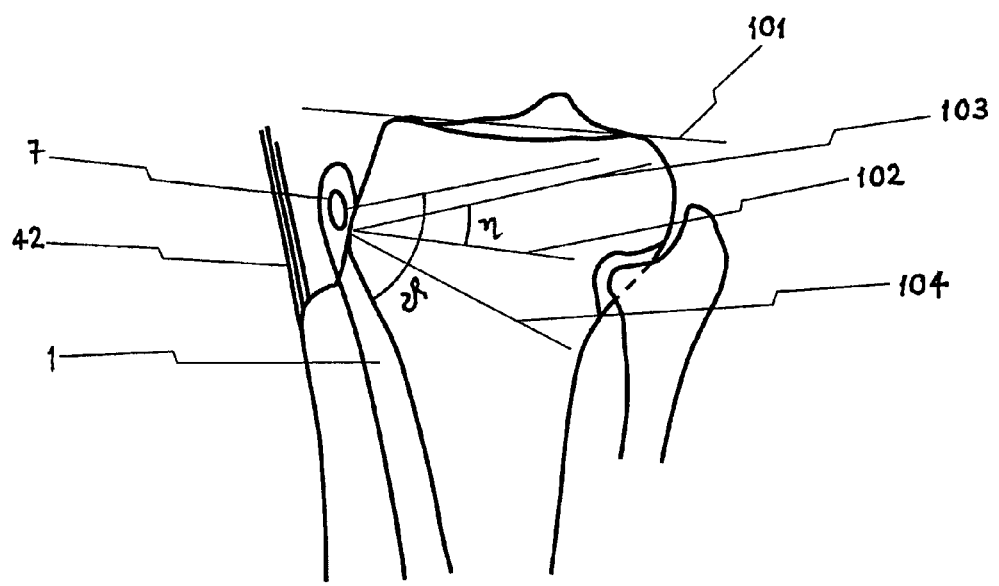
Figure 8:
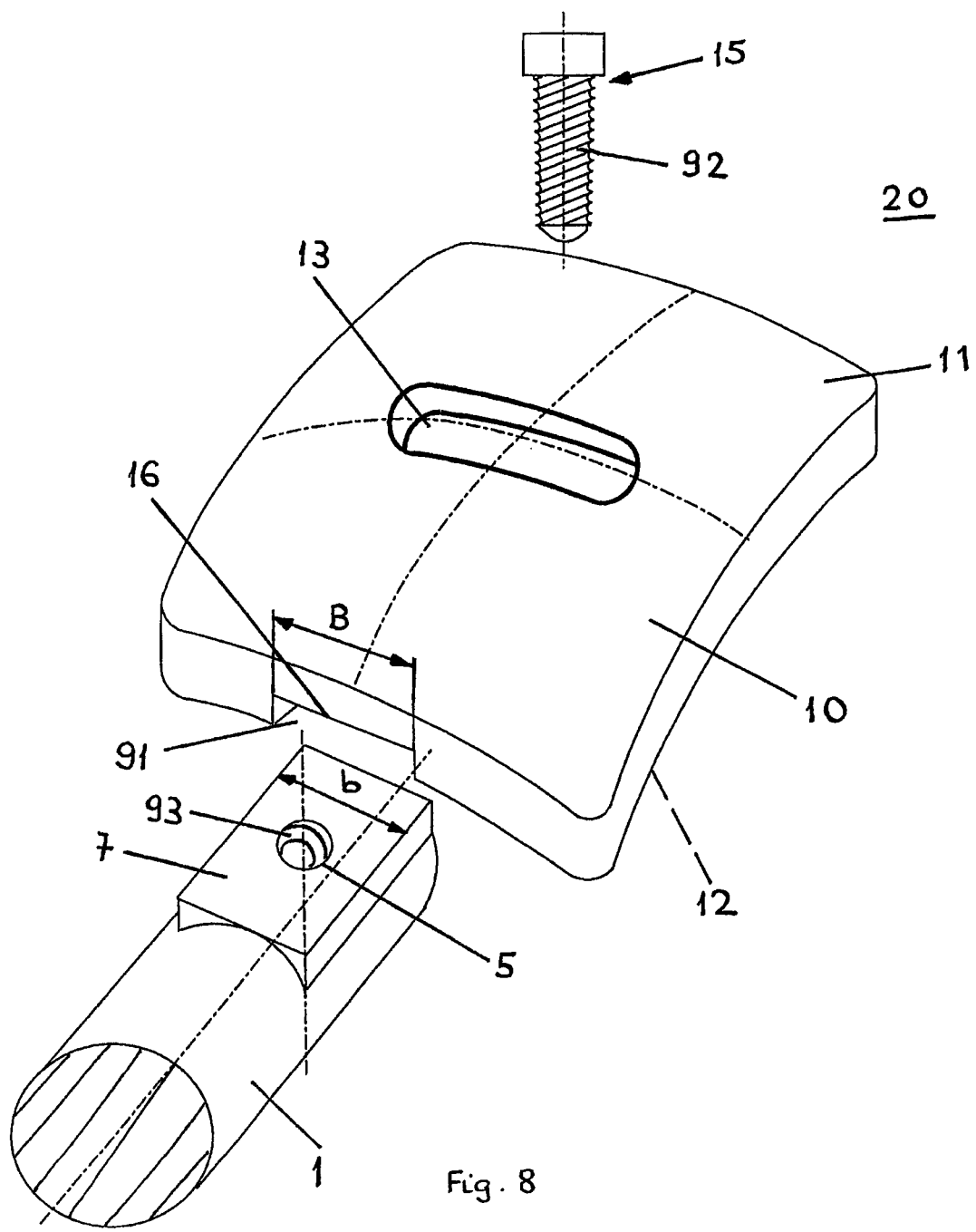

The invention and further developments of the invention will in the following, with the aid of partially simplified illustrations of several examples of embodiments, be explained in even further detail. These show:

FIG. 1a a simplified perspective view of a form of embodiment of the bone fixing device according to the invention;

FIG. 1b a simplified illustration of the planes corresponding to the clamping faces;

FIG. 1c an alternate perspective view of a form of embodiment of the bone fixing device according to the invention;

FIG. 2a a perspective view of a form of embodiment of the implant for the fixation of bones according to the invention;

FIG. 2b an alternate perspective view of a form of embodiment of the implant for the fixation of bones according to the invention;

FIG. 3 a perspective view of a further form of embodiment of the implant for the fixation of bones according to the invention;

FIG. 4A a simplified illustration of a form of embodiment of the bone plate according to the invention;

FIG. 4B a simplified illustration of another form of embodiment of the bone plate according to the invention;

FIG. 4C a simplified illustration of one more form of embodiment of the bone plate according to the invention;

FIGS. 5A-5E simplified illustrations of the fixing sectors of the endosteal fixing elements in the axial plane of the high tibial;

FIG. 6 a simplified illustrations of the fixing sectors of the endosteal fixing elements in the sagittal plane;

FIGS. 7A-7E simplified perspective illustrations of various forms of embodiment of the fixing mechanism between the bone plate and the intramedullary nail of the bone fixing device according to the invention; and FIG. 8 an exploded view of a further form of embodiment of the implant according to the invention.

FIG. 1 describes a form of embodiment of the bone fixing device fitted with an intramedullary nail 1 of a bone plate 10 and a compressing mechanism 9 for the fixing of the bone plate 10 to the intramedullary nail 1. The intramedullary nail 1 comprises a distal end part 2, a proximal end part 3, a central line 4 and a bore 5 with a bore axis 6 suitable for a rotating axis, extending across the central line 4 in the proximal end part 3. The bone plate 10 is provided with an upper side 11 and a lower side 12 destined for bone contact, and comprises a central continuous opening 13 set in the central section of the bone plate 10 and connecting the upper side 11 with the lower side 12, and several also continuous plate holes peripherally arranged around the opening 13.

A nail-side clamping face 7 is also conformed at the proximal end part 3 of the intramedullary nail 1, and the bone plate 10 has a plate-side clamping face 16 corresponding to the nail-side clamping face 7, where the two clamping faces corresponding to each other 7,16 are displaceable and rotatable against each other in an unclamped condition, meaning in an unlocked condition of the compression device 9, and fixed against each other in a clamped condition. In the form of embodiment shown in FIG. 1a the clamping face 7, 16 are conformed in a planar manner. The nail-side clamping face 7 lies in the area of the bore 5, while the plate-side clamping face 16 is defined by the lower side 12.

The two clamping faces 7, 16 corresponding to each other can be clamped to each other using a setscrew 15 capable of being passed through the central opening 13 and the bore 5, where the setscrew 20 can be anchored in the bone or in the bore by using a threaded connection. The clamping faces 7, 16 each have a toothed form as a tri-dimensional structuring system.

The planar, nail-side clamping face 7 lies in a plane B2 that is orthogonal to the bore axis 6 (ref. FIG. 1b). Moreover, a second plane B1 is defined by the center line 4—in case of a curved center line 4, by the tangent at the point of intersecting with the bore axis 6—and the diameter d of the intramedullary nail 1 running parallel to the plane B2. Depending on the form of embodiment of the nail-side and the plate-side clamping face 7, 16, the two planes B1; B2 intersect and enclose an angle alpha between each other, or the two planes B1; B2 are parallel or coinciding. In the form of embodiment shown in the FIG. 1, the two planes B1 and B2 are parallel and have a distance a to each other.

The FIG. 1b also illustrates a tri-dimensional system of coordinates whose z-axis runs coaxially to the center line 4 (FIG. 1a) of the intermedullary nail 1 in the area of the nail-side clamping face 7, or in case of an intramedullary nail 1 with a curved center line 4, tangentially through the point of intersection of the center line 4 with the bore axis 6 that forms the rotating axis. The x-axis runs orthogonally to the z-axis and coaxially to the diameter d of the intramedullary nail 1 that runs parallel to the plane 2.

The system shown in FIG. 2b for the endosteal and endomedullary fixing of bones comprises an orthopedic/traumatological base implant 20, known in the following as OTGI, that includes a bottom element 21 conformed as an intramedullary nail 1, a middle element 22 conformed as a bone plate 10 or as a base plate (BP), and a top element 23 consisting of a number of bone fixing elements 25. The form of embodiment shown here provides for three bone fixing elements 25, whereof the first is set up laterally (L), the second centrally (Z) and the third medially (M).

The bone fixing elements 25 are arranged such that the projections of their longitudinal axes 24L, 24Z and 24M are set up in the X,Z-plane, the X,Y-plane and the Y, Z-plane (FIG. 1b) at an angle with respect to the x-axis (in the X, Y-plane), the z-axis (in the X,Z-plane) and the z-axis (in the Y, Z-plane.

The intramedullary nail 1 and the bone plate 10 are adapted to the outer shape and to the inner architecture of the upper tibial section (to the so-called epiphysis, metaphysis, apophysis and diaphysis of the proximal tibia and to the endomedullary form (intramedullary form) of the tibia, and in a scaled execution follow the internal and external form of the tibia, while leaving the ligamentum patellae 42, the antero-lateral muscle position, the distal attachment of the pes anserinus tendon intact to allow a stable endosteal, exosteal, endomedullary fixation of high tibial fractures, tibial fractures, high tibial osteotomies and tibial osteotomies.

The intramedullary nail 1 and the bone plate 10 come typically to rest behind (dorsally to) and under (subligamentary to) the ligamentum patellae. Thanks to the subligamentary position of the bone plate 10 or the base plate and the intramedullary nail 1, the ligamentum patellae 42 and Hoffa's fatty tissue body is treated carefully, and a secondary depression of the patella such as in case of a transligamentary access can most likely be prevented.

The form of embodiment of the implant 20 shown in FIG. 2b illustrates an orthopedic, traumatological base implant (OTGI), which consists of top-,middle and bottom sections 23, 22, 21 and is characterized in that the top section 23 consists of a number of endosteal fixing elements 25, which in this case embrace a lateral (L), a central (Z) and a medial (M) endosteal fixing element 25, where the middle section 22, also known as intermediate section, consists of an anatomically correct bone plate 10 or basis plate adapted to the soft tissues, which is fitted with plate holes 14 as receiving devices 28 for the endosteal fixing elements 25, as auxiliary receiving devices 29 for auxiliary fixing elements such as for instance bone screws, and as recesses 30 for adapting to soft tissue elements. The bone plate 10 also comprises a plate-side clamping face 16, in this case meaning a suitably designed finely structured face which is preferably designed as a finely toothed fixing device and engages with a reciprocally designed fixing device forming the nail-side clamping face 7, such that the plate-side clamping face 16 and the nail-side clamping face 7 are connected to each other in a rotationally form-locking manner. The last-mentioned fixing device is connected, preferably at a fixed angle, with the top section of the curved endomedullary power transmitter or endomedullary nail 1, respectively, where these fixing devices, meaning the nail-side clamping face 7 and the plate-side clamping face 16, are preferably designed around a rotating axis coinciding with the bore axis 6 (perpendicular to the drawing plane) which is designed at an angle alpha of 65° to 115°, preferably 90° to the shaft axis or central line 4, respectively, of the endomedullary power transmitter and are capable of rotating against each other and of being fixed at a rigid angle.

The implant 20 (OTGI) typically exhibits endosteal, proximally localized fixing elements 25, which are formed on the top section 23 and connected with the bone plate 10 or base plate set up in a retro- and paraligamentary way, which is fixed in a prevalently exosteal manner.

The middle section or base plate is in turn suitably connected with an endomedullary power transmitter or with an intramedullary nail 1, such that relative axis corrections, lateral deviations of their positions and lateral displacements as well as possible angle corrections between the proximal and distal fracture- and osteotomy fragments are possible. A fixing mechanism 8 (refer to FIG. 1) which is preferably designed as a finely toothed rotating pin/rotating table, allows these possibilities of correction and guarantees its stability, after a correction is provided with been performed, up to the point of bone consolidation.

The distance of the bone face to the lateral, cranial and medial boundary of the tuberositas tibiae is consciously chosen so as to allow a certain displaceability of the bone plate 10 with respect to the tuberositas tibiae.

FIG. 3 shows a further form of embodiment of the bone plate 10 or the base plate (2) of the implant (OTGI). The bone plate 10 is the middle section 22 that connects the endosteal proximal lateral (L), central (Z) and medial (M) fixing elements 25 of the top section 23 with the distal lower side 21, the endomedullary power transmitter, meaning the intramedullary nail 1 at a fixed angle, through a finely toothed fixing mechanism.

As shown in FIG. 3, the bone-resembling shape of the bone plate 10 or base plate follows the outer profile of the antero-lateral high tibial 61. The bone plate 10 or base plate preferably covers the ventral face of the antero-lateral high tibial 61 in a radius of 5 to 30 mm as measured from the center 62 of the tuberositas tibiae 47, the attachment of the ligamentum patellae 42 up to the lateral high tibial boundary 63, where the attachment area of the fascia of the antero-lateral muscle system 64 of the tibia lies. In a lateral upward direction this potential attaching area of the base plate is delimited by the Gerdy tuberculum 65 (tibial attachment area of the tractus iliotibialis). In an upward direction the emplacing area of the base plate is delimited by the ligamentum coronarium, the meniscus frontal horns 66 and Hoffa's fatty tissue body, in a medial downward direction by the attachment of the pes anserinus tendons 67, in a downward direction by the proximal boundary of the tuberositas tibiae 47, in a median direction by the median lateral ligament 68 and in a ventral direction by the ligamentum patellae 42. The finely toothed fixing mechanism 8 integrated in the base plate is preferably designed in a flat form, fitted with a rotating device 69 coaxial with the bore axis 6, which allows a relative displacement of the finely toothed fixing devices engaged with each other of the bone plate or base plate and of the endomedullary power transmitter or intramedullary nail 1 and which, after the necessary correction has been made, fastens the same at a fixed angle.

The FIGS. 4A-4C show a form of embodiment of the bone plate 10 of the base plate. The bone plate 10 essentially covers the areas free of direct soft tissue attachments of the proximal epi-, metaphysis of the tibial head 41, and lies behind the ligamentum patellae 42, which is left intact. The bone plate 10 embraces, in a manner carefully treating the attachments, the lateral 44, cranial 45 and medial 46 boundary of the bone attachment 43 of the ligamentum patellae 42 on the tuberositas tibiae, while guarding a certain distance to the same.

The profile of the bone plate 10 essentially follows the attachment geometry of the tuberositas tibiae 47, and is preferably designed, on the lateral 44 and cranial 45 boundaries of the tuberositas tibiae 47, with reception openings for a fixation of the proximal endosteal fixing elements (FIG. 3A).

In another form of embodiment, the bone plate 10 is designed so as to essentially embrace the lateral 44, cranial 45 and medial 46 boundary of the tuberositas tibiae 47, such that the endosteal fixing elements 25 are preferably inserted in a paraligamentary manner, meaning in a manner carefully treating the ligamentum patellae 42 (FIG. 48).

In another form of embodiment the bone plate 10 is designed such that the endosteal fixing elements 25 are suitably applied near the periphery and that a central opening 13 is set up in the central region of the bone plate 10, such that the bone plate 10 is suitably designed for a displaceable fixing mechanism 8 (FIG. 4C).

FIG. 4C shows the ligamentum patellae 42, under which the bone plate 10 lies, as represented in a proximal 51 and in a distal 52 split manner.

The FIGS. 5a-5E show the fixing sectors of the endosteal fixing elements 25 (FIG. 1) in the axial plane. The endosteal lateral (L), central (Z), medial (m) cranially or caudally situated endosteal fixing elements 25 are preferably designed as bushing and rod elements, such as for instance as bushings with pins insertable in the plate holes 14 (FIG. 1) that can be passed through the central bores of the same, and essentially inserted in the axial plane in a ventral to dorsal direction.

Figure 5A:
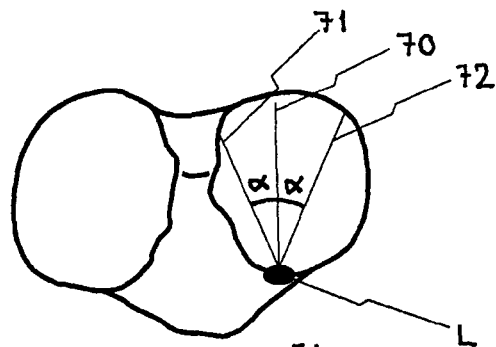

The lateral endosteal fixing element (L) is inserted into the subchondral region of the lateral femoro-tibial compartment so as to define, measured from the ventral entry position as compared to the orthogonal alignment in the antero-posterior direction from the zero position 70, a positioning sector in an angle alpha of plus/minus 25 degrees from central 71 to lateral 72, preferably with a deviation of plus/minus 5 degrees (FIG. 5A).

Figure 5B:
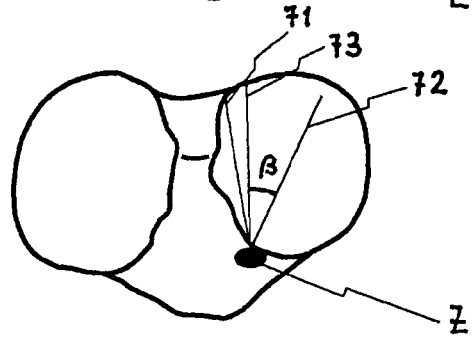

The central endosteal fixing element (Z) is, in the central region of the lateral femoro-tibial compartment, suitably inserted in a ventro-dorsal direction subchondrally in reference to the zero-position axis 73, with a possible positioning deviation at an angle beta toward central 71 of 20 degrees, and toward lateral 72 of 35 degrees, according to FIG. 5B.

Figure 5C:
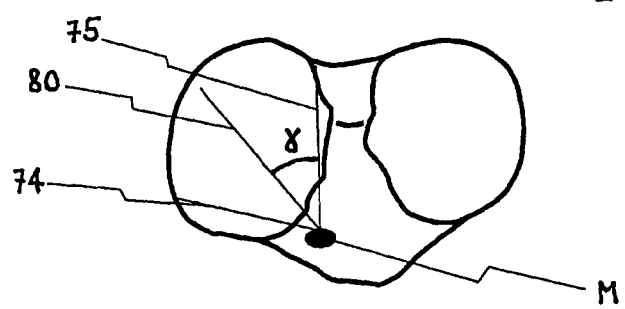

The medial endosteal fixing element (M) is preferably inserted subligamentary from an antero-lateral direction, as compared to a zero axis 80 obliquely oriented from an antero-lateral to a postero-medial direction, with an angle deviation gamma of 35 degrees toward ventral 74 and of 45 degrees toward dorsal-central 75 in the subchondral region of the medial femoro-tibial compartment (FIG. 5C).

Figure 5D:
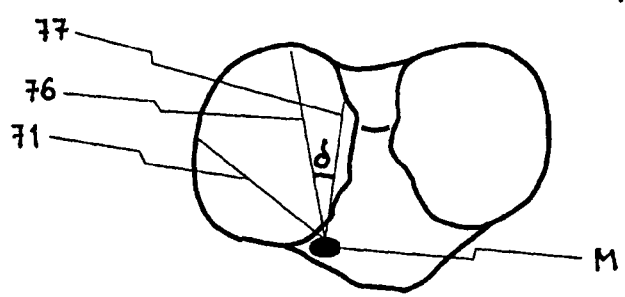

In a further form of embodiment, the medial endosteal fixing element (M) is paraligamentary inserted from a ventral direction into the subchondral region of the medial femoro-tibial compartment so as to define, from the ventro-dorsally aligned zero-position 76, an angle deviation delta of 45 degrees toward medial 77 and up to 20 degrees toward central 71, preferably plus/minus 5 degrees (FIG. 5D).

Figure 5E:
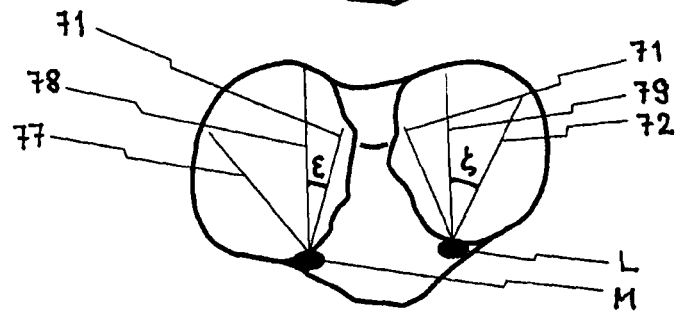

In an additional form of embodiment at least two endosteal lateral (L) and two endosteal medial (M) fixing elements are each paraligamentary inserted from ventral lateral and ventral medial, preferably subchondrally in an antero-posterior direction so as to define, in reference to a ventro-dorsally aligned medial zero-axis 78, an angle deviation epsilon of 30 degrees toward medial 77 or of 25 degrees toward central 71, preferably of 0 degrees, with a deviation of 5 degrees in each direction, and in reference to a ventro-dorsally aligned lateral zero-axis 79, an angle deviation zeta of 30 degrees toward lateral 72 and of 30 degrees toward central 71, preferably of 0 degrees, in each case with a deviation of 5 degrees (FIG. 5E).

FIG. 6 shows the fixing sectors of the endosteal fixing elements in the sagittal plane. The endosteal lateral (L), central (Z) and medial (M) fixing elements 25 (not drawn here) are in the sagittal plane essentially aligned in a subchondral manner parallel to the individual dorsal slope of the medial and lateral tibial plateau 101 and form, in reference to the sagittaly aligned antero-posterior zero-axis 102, an angle deviation aeta of 25 degrees toward cranial 103 and of 45 degrees toward caudal 104. The angle theta is preferably designed as an angle theta of 0 to 90 degrees plus/minus 5 degrees toward the nail-side clamping face 7 ("fixing mechanism") of the endomedullary power transmitter set up under the ligamentum patellae, meaning the intramedullary nail 1.

The FIGS. 7A, 7B, 7C, 7D 7E show the suitable fixing mechanisms between the base plate (BP) on one hand and the endomedullary power transmitter (EMKT) on the other hand. Alternative Embodiment of a Fixing Mechanism with a Finely Toothed Face Structure Designed in the Form of a Plate (FIG. 7A):

In this form of embodiment the reciprocal fixing mechanism is preferably conformed as a plate 8, such that the suitably finely toothed fixing face of the bone plate 10 or base plate with the similarly structured fixing face of the endomedullary power transmitter or intramedullary nail 1 is, when the fixing faces are subjected to pressure, acting through a compression mechanism 9 to achieve a mutual fixation of the faces at a fixed angle.

Alternative Embodiment of a Finely Toothed Fixing Mechanism Designed in a Convex-Concave Form (FIG. 7B):

In this form of embodiment the fixing mechanism of the face of the bone plate 10 or of the base plate is designed in a finely toothed manner and formed with a plate-side clamping face 16 preferably convexly curved toward ventral for a stable fixation with fine teeth 140 which engages in the reciprocal, finely teethed nail-side clamping face 7 designed in a concave manner toward dorsal on the bottom face 150 of the intramedullary nail 1, or in the endomedullary power transmitter.

Alternative Embodiment of a Finely Toothed Fixing Mechanism Designed in a Flat-Flat Form (FIG. 7C):

In this form of embodiment the fixing mechanism of the top bone plate 10' and of the bottom bone plate 10" is designed in a finely toothed manner and preferably formed in a flat manner toward ventral for a stable fixation, such that these plates engage in the reciprocal, finely toothed fixing mechanism 8 designed in a flat form toward dorsal and ventral of the intramedullary nail 1 or of the intramedullary power transmitter: this is a finely toothed, displaceable fixing mechanism that subjects the finely toothed faces to engage with each other by subjecting them to pressure through a compression device 9 designed toward central.

The FIG. 7D shows an intramedullar nail 1 and a bone plate 10 with a bushing-like appendix 110 designed to pass an endosteal bone fixing element 25 through the central opening 13. The nail-side and the plate-side clamping face 7; 16 are also curved, where the nail-side clamping face 7 is convex and the plate-side clamping face 16 is curved in a correspondingly concave manner.

The FIG. 7E shows a form of embodiment comprising an intramedullary nail 1 with a proximal end part 3 conformed like a fork, and a bone plate 10 arranged between the two prongs of the fork 120; 121. The compression device 9 to fix the bone plate 10 to the intramedullary nail 1 in this case essentially comprises a setscrew 15 which is passed through the bore 5 in the second prong of the fork 121 of the intramedullary nail 1 and the central opening 13 in the bone plate 10, and can be fixed in a corresponding internal thread 130 in the first prong of the fork 120.

The FIG. 8 shows a form of embodiment of the bone fixing device 20 with a spherically curved bone plate 10. The bone plate 10 comprises on its lower side 12 a groove 91 of a width B, whose groove bottom forms the plate-side clamping face 16. The groove 91 is for this purpose conformed such that the groove bottom is a flat face. The groove bottom can, depending on the requirements, be formed in a flat manner over only part of its length. The nail-side clamping face 7 of the intramedullary nail 1 is provided with a width b<B, such that the nail-side clamping face 7 is displaceable with respect to the plate-side clamping face 16. The bone plate 10 also comprises a central opening 13 which is continuous from the top side 11 to the bottom side 12, and is suitable for receiving the screw shaft 92 of a setscrew 15. The bore 5 in the intramedullary nail 1 is fitted with an internal thread 93, such that the setscrew 15 can be screwed into the bore 5. The setscrew 15 forms, together with the threaded connection formed by the internal thread 93, the compression device 9 for clamping the nail-side and the plate-side clamping faces 7, 16.

In the following, a possible operating technique for the bone fixing device is described in order to better highlight its function. The operating technique is described in the example of a tibia.

Operating Technique

1. Performing a lateral incision of the ligamentum patellae, which is provided with the advantage of not destroying the stretching mechanism.
2. Setting up a core-drilling in the prevalently antero-posterior direction, parallel to the individual slope of the tibial plateau in the sagittal plane. The bore axis 6 corresponds at the same time to the later rotating axis between the intramedullary nail 1 and the bone plate 10. The localization occurs outside the soft tissue attachments, from the central to the medial section of the lateral high tibial in the vicinity of the former growth suture line (proximal tibial epiphysis line) up to the rear side corticalis.
3. Drawing and storing of the bone cylinder thus formed.
4. Establishing an incomplete, horizontal bone weakening section starting from the coring bore and proceeding toward lateral, above the proximal tibio-fibular joint, at a sufficient distance to the subchondral bone plate of the lateral high tibial.
5. Performing an incomplete undercut of the tuberositas tibiae, which remains essentially connected to the lateral column of the tibia.

6. Establishing a second coring bore starting from the first coring bore, which is essentially directed toward the intramedullary hollow.
7. Drawing and storing of the bone cylinder thus formed.
8. Inserting of a centering drill bushing into the second coring bore, such that the sloping plane of the programmed bone weakening section and the slope of the same with respect to the longitudinal axis of the tibia can be defined, preferably under imaging control.
9. Performing an incision in the region of the postero-medial tibial rounding.
10. Scraping off the periosteum over a short length.
11. Driving the cutting tools according to the established coring bores.
12. Creating a bone opening or an incomplete bone fissure in the region of the planes set up by the weakened bone sections.
13. Checking the mechanical leg axis, defined as being the joining line between the hipbone head center and the upper ankle joint center, such that the force vector crossing the knee joint is shifted from the damaged knee joint compartment to the undamaged or less damaged knee joint compartment by gradually expanding the bone sections.
14. After concluding a verification of the extension of the new mechanical leg axis, fixing of the relative position of the expanded bone sections one against the other, until the bones are safely consolidated through the bone fixing device according to the invention.

As concerns the procedural steps 2-8, these are preferably done while checking the position and alignment of the first coring bore by using imaging fluoro-navigation, landmark-specific and computer-assisted technologies.

Other variants of bone weakening consist in a Z-shaped bone weakening for a left-sided tibia.

The invention claimed is:

1. A bone fixing device comprising:
   an intramedullary nail with a distal end part, a proximal end part, a center line and a bore extending in the proximal end part across and transverse to the center line, provided with a bore axis; and
   a bone plate with a top side, a bottom side destined for bone contact, a central continuous opening set up in a central section of the bone plate and connecting the top side with the bottom side and several plate holes, peripherally arranged around the central opening and also continuous, wherein
   at least one nail-side clamping surface is conformed at the proximal end part of the intramedullary nail,
   the bone plate is provided with at least one plate-side clamping face corresponding to the nail-side clamping surface such that
   the two clamping surfaces corresponding to each other are displaceable and rotatable against each other in an unclamped condition, and fixed to each other such that areal surface portions of each clamping surface are in contact with each other in a clamped condition, and
   the center line intersects the nail-side clamping surface under an average angle of 1° to 20°.

2. The bone fixing device according to claim 1, wherein the bone fixing device further comprises a compression device whereby the nail-side and the plate-side clamping surfaces can be pressed against each other.

3. The bone fixing device according to claim 2, wherein the compression device comprises an internal thread in the bore and a setscrew capable of being passed through the central opening and screwed into the internal thread of the bore.

4. The bone fixing device according to claim 1, wherein the intramedullary nail is provided with two nail side clamping surfaces.

5. The bone fixing device according to claim 4, wherein the two nail-side clamping surfaces are arranged in an essentially asymmetric, eccentric form with regard to the center line.

6. The bone fixing device according to claim 1, wherein the nail-side clamping surface is conformed in a flat manner and defines a first plane, which forms an angle alpha of 10° to 20°, with a second plane defined by the center line and a diameter d, extending parallel to the first plane of the intramedullary nail.

7. The bone fixing device according to claim 6, wherein a z-axis—in an intramedullary nail with a curved center line—is formed by the tangent to the center line at the intersection of the center line with the bore axis that forms a rotating axis.

8. The bone fixing device according to claim 1, wherein a first plane set orthogonally to the bore axis forms an angle alpha of 0° to 30° with a second plane defined by a diameter d of the intramedullary nail extending through the central line and parallel to the first plane.

9. The bone fixing device according to claim 1, wherein a first plane set orthogonally to the bore axis extends parallel to a second plane defined by a diameter d extending through the center line and parallel to the first plane.

10. The bone fixing device according to claim 1, wherein the nail-side clamping surface is set in the region of the bore.

11. The bone fixing device according to claim 1, wherein the plate-side clamping surface is conformed on the bottom side of the bone plate.

12. The bone fixing device according to claim 11, wherein both the top side and the bottom side of the bone plate have a plate-side clamping surface.

13. The bone fixing device according to claim 1, wherein the plate-side clamping surface is conformed on the top side of the bone plate.

14. The bone fixing device according to claim 1, wherein the plate-side clamping surface is conformed inside the bone plate and extends essentially parallel to its bottom and top side.

15. The bone fixing device according to claim 1, wherein the plate-side clamping surface is conformed in the region of the opening.

16. The bone fixing device according to claim 1, wherein the center line intersects the nail-side clamping surface under an average angle of 2° to 10°.

17. The bone fixing device according to claim 1, wherein the proximal end part of the intramedullary nail is conformed as a separate, modular construction element.

18. The bone fixing device according to claim 1, wherein the intramedullary nail is curved in an unsymmetrical, multi-planar manner.

19. The bone fixing device according to claim 1, wherein the clamping surfaces corresponding to each other are each conformed in a planar, spherical or cylindrical manner.

20. The bone fixing device according to claim 1, wherein the clamping surfaces have a tri-dimensional structure.

21. The bone fixing device according to claim 20, wherein the tri-dimensional structure is in the form of toothings that are conformed as rounded windings, pyramidal tips or multilayered polygons.

22. The bone fixing device according to claim 1, wherein a distal terminal parabola of the intramedullary is symmetrically rounded.

23. The bone fixing device according to claim 1, wherein the intramedullary nail is provided with at least nine longitudinal grooves arranged in a planar parallel manner.

24. The bone fixing device according to claim 1, wherein a distal extremity of the intramedullary nail is longitudinally split.

25. The bone fixing device according to claim 1, wherein the bone plate is provided with a concave, curved bottom side.

26. The bone fixing device according to claim 25, wherein the bottom side and the top side are conformed in a spherically curved manner.

27. The bone fixing device according to claim 1, wherein the bone plate is provided with a convex, curved top side.

28. The bone fixing device according to claim 1, wherein the bottom side of the bone plate is provided with a groove with a groove bottom forming the plate-side clamping face, a first and a second lateral wall, and that the groove between the first and the second lateral wall is provided with a minimum width b, which allows an at least partial reception of the proximal end part of the intramedullary nail in the region of the nail-side clamping face such that the nail-side clamping face rests against the plate-side clamping face.

29. The bone fixing device according to claim 28, wherein the proximal nail terminal of the intramedullary nail is provided with a width B>b in the region of the nail-side clamping face.

30. The bone fixing device according to claim 1, wherein the bone fixing device comprises a bone fixing element with at least one longitudinal axis.

31. The bone fixing device according to claim 30, wherein the at least one bone fixing element is arranged such that the projections of its longitudinal axis in an X,Z-plane, an X,Y-plane and an X,Z-plane of a tri-dimensional system of coordinates with axes x,y,z in relation to the x-axis (in the X,Y-plane), to the z-axis (in the X,Z-plane) and to the z-axis (in the Y,Z-plane) enclose an angle between 0° and 60°, where the z-axis extends coaxially to the center line of the intramedullary nail in the region of the nail-side clamping surface, and the x-axis extends orthogonally to the z-axis and coaxially to the diameter d of the intramedullary nail.

32. The bone fixing device according to claim 30, wherein the face of the intramedullary nail, of the bone plate and of any other bone fixing elements is spark-anodized.

33. The bone fixing device according to claim 30, wherein the face of the intramedullary nail of the bone plate and of any other bone fixing elements is fitted with a microbiocidal coating.

34. The bone fixing device according to claim 30, wherein the bone fixing elements are conformed as intramedullary wires.

35. The bone fixing device according to claim 30, wherein the bone fixing elements comprise bushings pressed into receptacles in the bone plate, whose central bores allow continuous bone screws.

36. The bone fixing device according to claim 1, wherein the intramedullary nail is conformed in an asymmetrical manner.

37. The bone fixing device according to claim 1, wherein the intramedullary nail is provided with a first curvature in a first (frontal or latero-medial) plane, and a second curvature in a (sagittal or antero-posterior) plane perpendicular to the first plane.

38. The bone fixing device according to claim 1, wherein the device also comprises one or more of the following construction elements as bone fixing elements:
- a pushing screw
- a pulling screw
- a compressing screw
- a setscrew.

39. The bone fixing device according to claim 1, wherein the intramedullary nail is provided with a continuous channel.

40. The bone fixing device according to claim 1 wherein the intramedullary nail is made of one piece.

* * * * *